United States Patent [19]
Kuriyama

[11] Patent Number: 5,728,577
[45] Date of Patent: Mar. 17, 1998

[54] STIRRED TANK BIOREACTOR

[76] Inventor: Kiyoshi Kuriyama, c/o Kyoto Suiken Co., Ltd. 82-4, Kitazono-cho, Shimogamo, Sakyo-ku, Kyoto-shi, Kyoto-fu, Japan

[21] Appl. No.: 699,357

[22] Filed: Aug. 19, 1996

[30] Foreign Application Priority Data

Aug. 22, 1995 [JP] Japan ................................ 7-213701

[51] Int. Cl.$^6$ ........................................... C12M 1/02
[52] U.S. Cl. ............................ 435/299.1; 435/297.3; 435/298.1; 210/619; 210/150
[58] Field of Search .................. 435/297.1, 297.2, 435/297.3, 298.1, 299.1; 210/150, 615, 619, 618

[56] References Cited

U.S. PATENT DOCUMENTS

| 4,310,630 | 1/1982 | Girard et al. ............... 435/299.1 |
| 4,678,567 | 7/1987 | Ueda ........................ 210/615 |

FOREIGN PATENT DOCUMENTS

| 0 253 774 | 1/1988 | European Pat. Off. ......... 435/299.1 |
| 52-35455 | 3/1977 | Japan ........................ 210/150 |
| 59-179061 | 10/1984 | Japan ..................... 435/299.1 |
| 62-083099 | 4/1987 | Japan ..................... 435/299.1 |
| 1-111489 | 4/1989 | Japan ........................ 210/150 |
| 2-122895 | 5/1990 | Japan ........................ 210/150 |
| 2-203780 | 8/1990 | Japan . |
| 916435 | 4/1982 | U.S.S.R. ..................... 210/150 |
| 1710522 | 2/1992 | U.S.S.R. ..................... 210/150 |

*Primary Examiner*—William H. Beisner
*Attorney, Agent, or Firm*—Dennison, Meserole, Pollack & Scheiner

[57] ABSTRACT

A bioreactor includes a treatment tank for receiving liquid to be treated, at least one carrier member having a carrier body formed of porous materials and immobilized with nonagglutinative microorganisms for treating the liquid, and a drive unit for moving the at least one carrier member in the treatment tank.

10 Claims, 12 Drawing Sheets

STIRRED TANK BIOREACTOR

BACKGROUND OF THE INVENTION

1. Field of the Invention

The present invention relates to a bioreactor suitable for treating or fermenting liquid containing stuff materials, or treating or purifying liquid containing pollutant materials such as household sewage and industrial sewage, and more particularly to a bioreactor suitable for biologically treating desired liquid containing various materials in which carrier members immobilizing microorganisms thereon are preferably moved to increase contact efficiency between the microorganisms immobilized on the carrier members and liquid to be treated.

2. Description of the Prior Art

Figure 15:
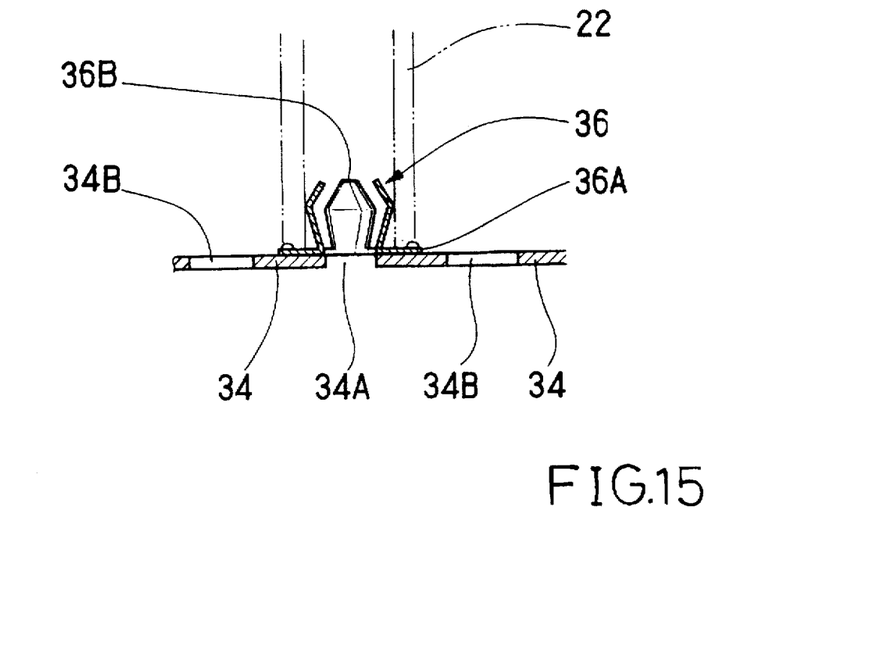
FIG. 15 is a sectional view taken along line XV—XV of FIG. 14.

FIG. 15 exemplarily shows a conventional bioreactor for treating effluent or sewage by utilizing nonagglutinative microorganisms such as yeasts. The bioreactor is constituted mainly of a fluidized bed type treatment tank 102 having an inlet port 108 and an outlet port 109, and a desired amount of carrier chips 101 each immobilizing the nonagglutinative microorganisms as cultured. The treatment tank 102 has a treatment cavity 102a formed between the inlet port 108 and the outlet port 109. The carrier chips 101 are freely movably received in the treatment cavity 102a. Each of the inlet and outlet ports 108 and 109 is covered with a net 103 to confine the carrier chips 101 in the treatment cavity 102a. The inlet and outlet ports 108 and 109 communicate with an sewage feed pipe or inlet pipe 106 and a treated sewage drainage pipe or outlet pipe 107, respectively. Further, the treatment tank 102 is provided with an air feed pipe 104 introduced into the treatment cavity 102a for producing air bubbles 105 in the sewage fed into the treatment cavity 102a.

In the bioreactor, the sewage is fed into the treatment cavity 102a of the treatment tank 102 through the inlet pipe 106, and simultaneously, air is fed into the cavity through the air feed pipe 104 so as to produce the air bubbles 105 in the sewage for agitation. As a result, the sewage is treated in the treatment cavity 102a by the microorganisms immobilized on the carrier chips 101. The sewage as treated is then discharged through the outlet pipe 107.

Figure 16:
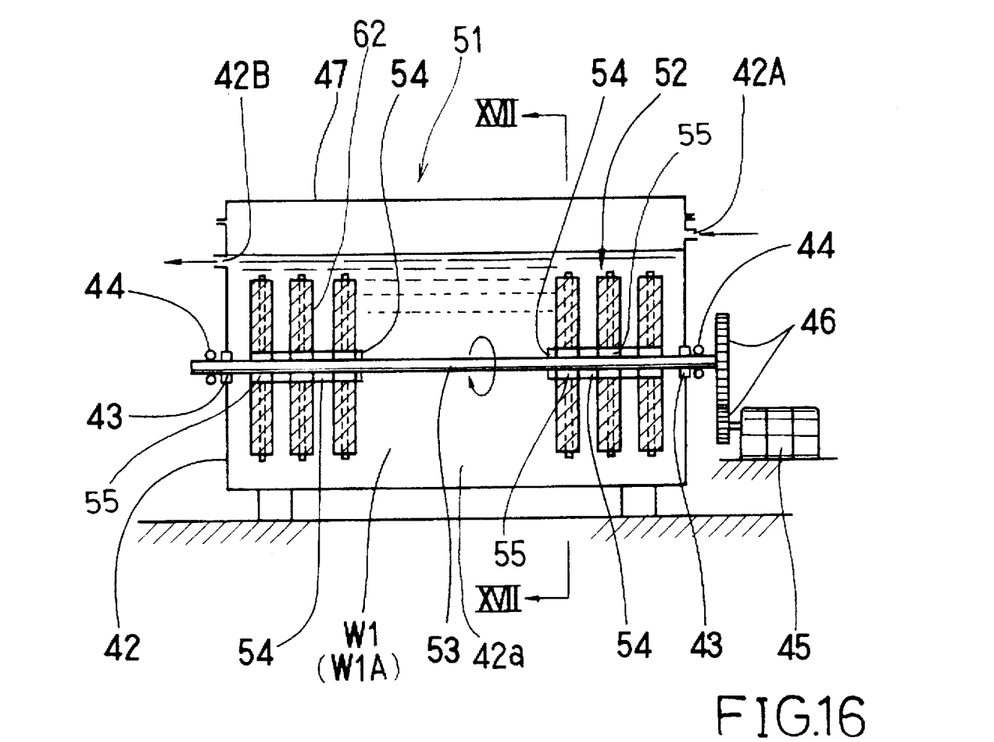
FIG. 16 is a vertically sectional view of a bioreactor according to a second embodiment of the present invention.

FIG. 16 exemplarily shows another conventional bioreactor for treating sewage by utilizing nonagglutinative microorganisms. The bioreactor is constituted mainly of a fixed bed type treatment tank 112 having an inlet port 118 and an outlet port 119, and a desired amount of carrier chips 111 each immobilizing the nonagglutinative microorganisms thereon. The treatment tank 112 has a treatment cavity 112a formed between porous plates 113 provided in the inlet and outlet ports 118 and 119. The carrier chips 111 are closely and water flowably packed in the treatment cavity 112a. The inlet and outlet ports 118 and 119 communicate with an sewage feed pipe or inlet pipe 116 and a treated sewage drainage pipe or outlet pipe 117, respectively. Further, the treatment tank 112 is provided with an air feed pipe 114 introduced into the inlet ports 118 for agitating the sewage to be treated.

In the bioreactor, the sewage is fed into the treatment cavity 112a of the treatment tank 112 through the inlet pipe 116. The sewage is treated in the treatment cavity 112a by the microorganisms immobilized on the carrier chips 111. The sewage as treated is then discharged through the outlet pipe 117.

However, in the conventional bioreactors as described above, the microorganisms immobilized on the carrier chips do not uniformly contact the swage to be treated. This may lead insufficient contact efficiency between the microorganisms immobilized on the carrier chips and the sewage, thereby causing poor effectiveness or treatment capacity of the bioreactor.

SUMMARY OF THE INVENTION

It is an object of the invention to provide a bioreactor which may increase effective contact rate or contact efficiency between immobilized nonagglutinative microorganisms and liquid to be treated.

In order to attain the object, the present invention provide a bioreactor including a treatment tank for receiving liquid to be treated, a carrier member having a carrier body formed of porous materials and immobilized with nonagglutinative microorganisms for treating the liquid, and a drive unit for moving the carrier member in the treatment tank.

The bioreactor may increase contact efficiency between the immobilized microorganisms and the liquid to be treated, thereby increasing treatment power thereof.

The drive unit may include a support unit retaining the carrier member thereon. Further, the carrier member may be detachably connected to the support unit. With this construction, the carrier member can be easily replaced with a new one.

The carrier member may include a reinforcement member to prevent deformation of the carrier body. With this construction, the carrier body is sustained so as not to be deformed. This permits easy handling of the carrier member. Also, the carrier member can be moved in the liquid without accompanying deformation of the carrier body.

The present invention will become more fully apparent from the claims and the description as it proceeds in connection with the drawings.

DETAILED DESCRIPTION OF THE PREFERRED EMBODIMENTS

Preferred embodiments of the present invention will now be described in detail with reference to the drawings.

Figure 1:
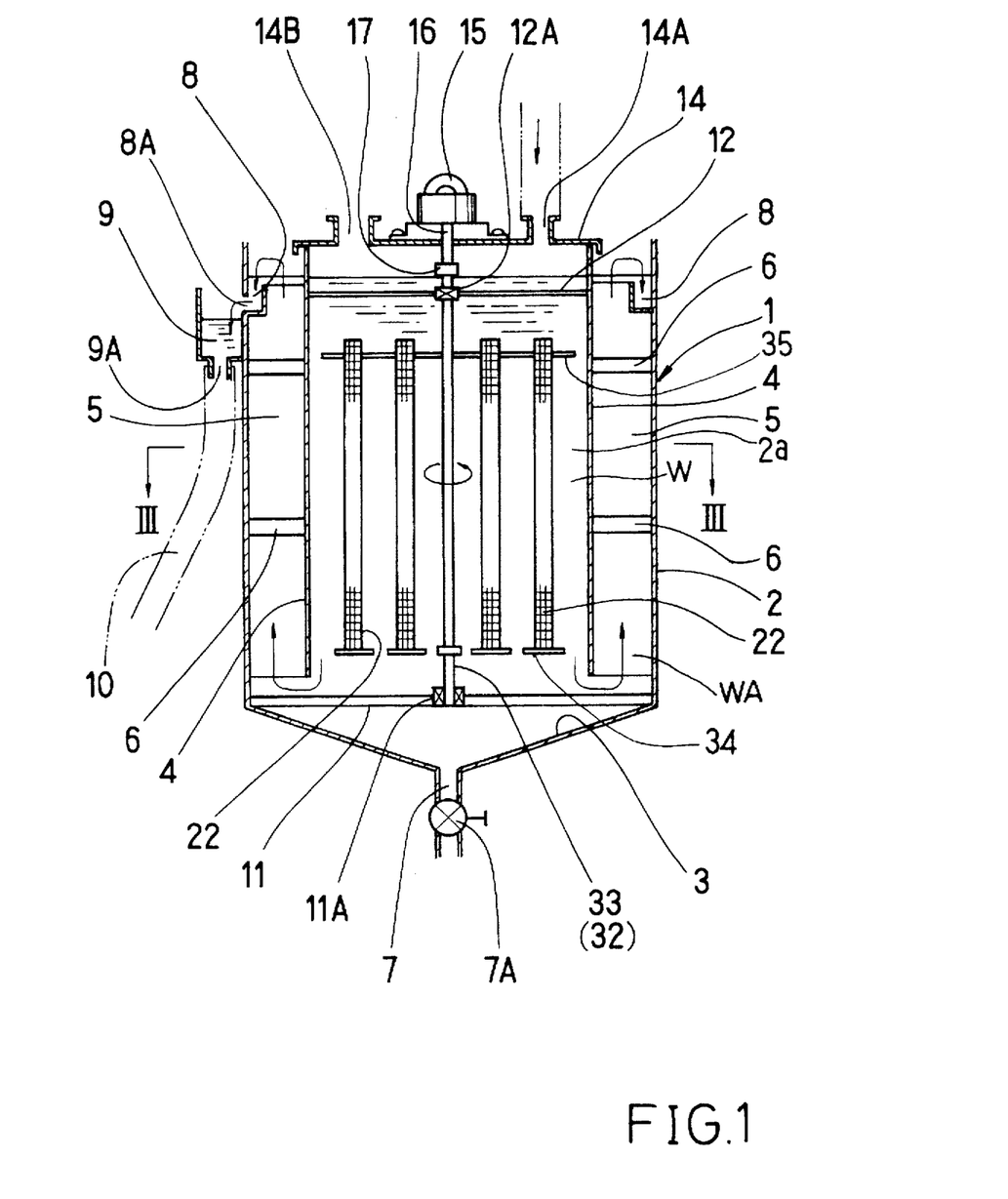
FIG. 1 is a vertically sectional view of a bioreactor according to a first embodiment of the present invention.
Figure 2:
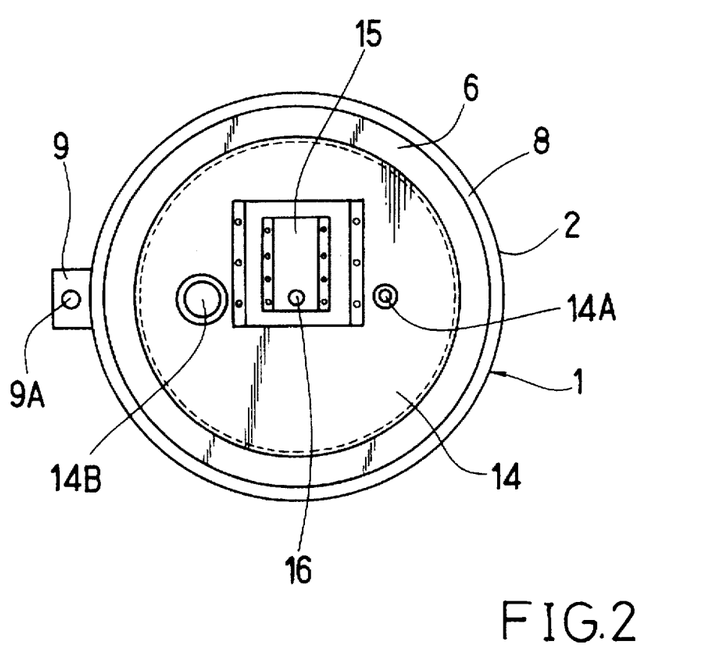
FIG. 2 is a plan view of FIG. 1.

Referring to FIGS. 1 to 15, shown therein is a first embodiment of the invention. As shown in FIG. 1, a bioreactor 1 is constituted mainly of a cylindrical treatment tank 2, an inner cylinder 4 received substantially concentrically in the treatment tank 2 and having a treating cavity 2a into which liquid W to be treated is introduced, a plurality of tubular carrier members 22 immobilized with microorganisms and located in the treating cavity 2a, and a drive unit 32 for retaining the carrier members 22 and rotating the same along orbital paths in the treating cavity 2a. Further, it is to be noted that the liquid W may be, for example, waste water containing pollutant materials to be purified, water containing organic stuff materials to be fermented, and water containing precursors to be treated for producing medical products.

As best shown in FIG. 1, the treatment tank 2 includes a funnel-shaped bottom wall 3 having a central drain port 7 provided with a drain valve 7a. Further, the inner cylinder 4 is fixed to the treatment tank 2 by a plurality of retainer pieces 6 and is dimensioned so that an annular flow passage 5 is formed between the inner cylinder 4 and the treatment tank 2. Additionally, the inner cylinder 4 is detachably provided with a cover plate 14 having an inlet port 14A through which the liquid W is introduced into the treating cavity 2a and having a vent port 14B.

The treatment tank 2 is provided with an over-flow type annular outlet channel 8 circumferentially extending along an inside surface of an upper end portion thereof. The treatment tank 2 has an outlet port 8A communicating with the outlet channel 8. The outlet port 8A is provided with a hopper 9 having an exit port 9A to which a conduit pipe 10 is connected.

The treatment tank 2 is fixedly received with lower intersecting frame members 11 which have a bearing member 11A mounted on the intersection thereof. Further, the inner cylinder 4 is fixedly received with upper intersecting frame members 12 which have a bearing member 12A mounted on the intersection thereof.

The drive unit 32 includes a stem 33 as a support unit received in the treating cavity 2a, an upper support disk 35 as the support unit mounted on an upper section of the stem 33, and a lower support disk 34 as the support unit mounted on a lower section of the stem 33. The stem 33 is rotatably supported by the bearing members 11A and 12A at the upper and lower ends thereof. The drive unit 32 also includes a power unit or motor 15 mounted on the cover plate 14 and having a drive shaft 16 which projects downwardly through a central bore 14C formed on the cover plate 14. The drive shaft 16 is coupled to the stem 33 through a coupling 17 mounted thereon. As is well known, the coupling 17 has a square hole (not shown) into which a square head (not shown) formed on the stem 33 is unrotatably received.

Figure 3:
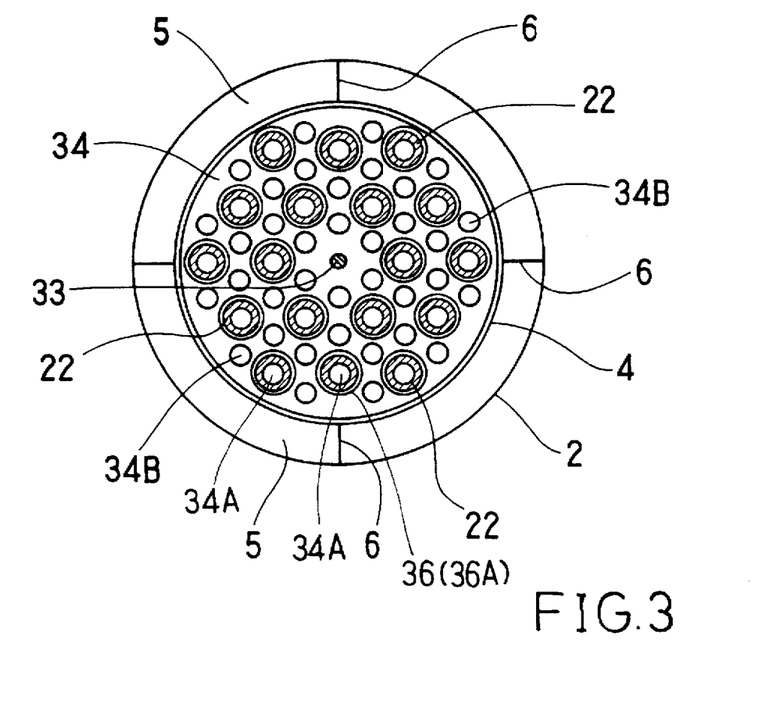
FIG. 3 is a sectional view taken along line III—III of FIG. 1.
Figure 14:
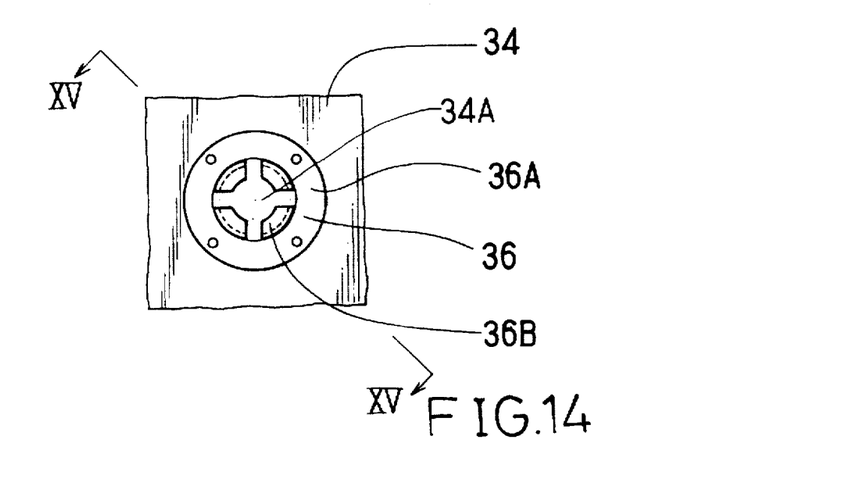
FIG. 14 is a partially enlarged plan view of a lower support disk of the drive unit.

As shown in FIGS. 3, 14 and 15, the lower support disk 34 is formed with a plurality (18 is shown for illustration purposes) of through holes 34A and a plurality of passage holes 34D, and is provided with a plurality of fixture members 36 for securing a lower section of the carrier members 22 thereon. As best shown in FIG. 3, the through holes 34A are arranged substantially symmetrically with the stem 33. Further, each through hole 34A has a diameter smaller than the inner diameter of the carrier member 22. The passage holes 34B are preferably located around the through holes 34A. As best shown in FIGS. 14 and 15, each fixture member 36 is positioned over the through hole 34A, and is constituted of an annular base portion 36A fixed on the upper surface of the lower support disk 34 and a slotted plug portion 36B connected integrally to the annular base 36A. As will be easily understood, the plug portion 36B elastically engages the inner circumferential surface of the carrier member 22, thereby securing the lower section of the carrier member 22 on the lower support disk 34. Further, the fixture member 36 is not limited to one having such a slotted plug portion 36B, and may be one having a tubular plug portion (not shown) if it can secure the carrier member 22 on the lower support disk 34.

Figure 4:
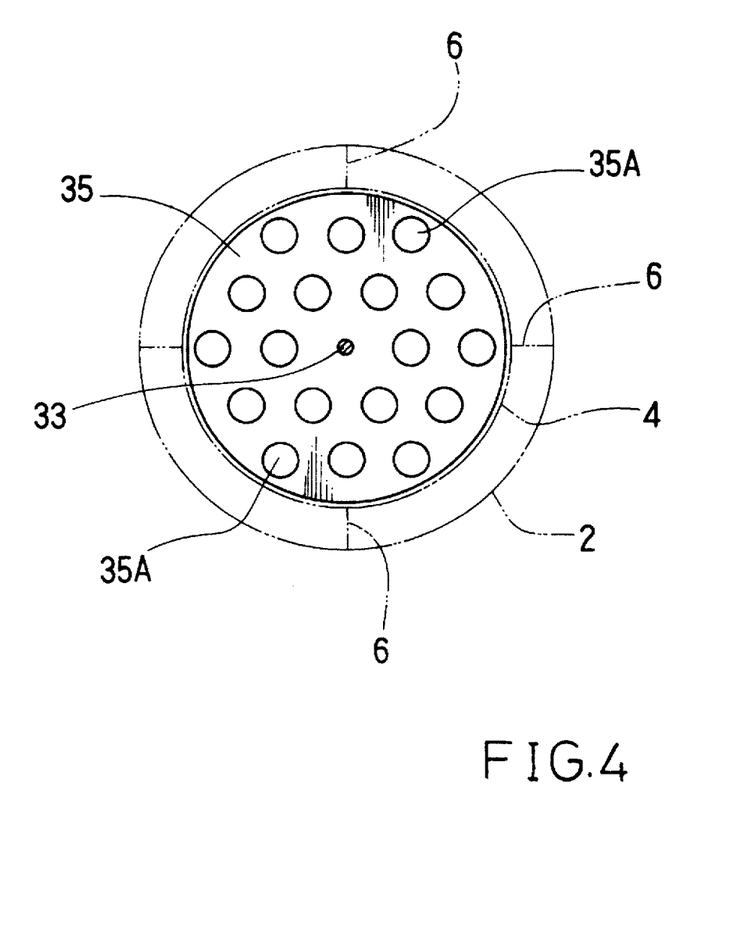
FIG. 4 is a plan view of an upper support disk of a drive unit used in the bioreactor.
Figure 5:
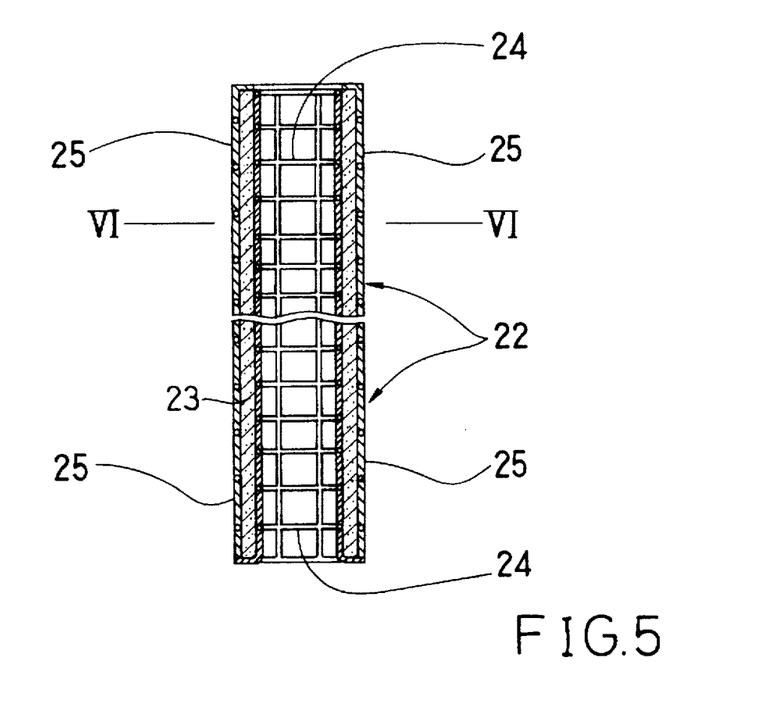
FIG. 5 is an enlarged vertically sectional view of a carrier member used in the bioreactor.
Figure 6:
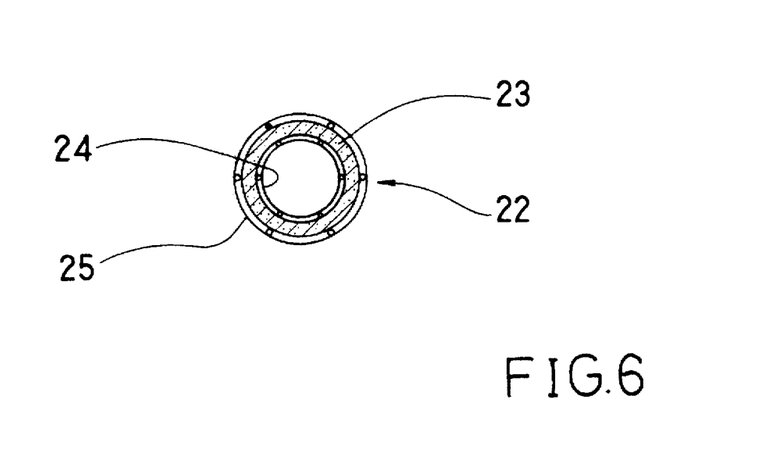
FIG. 6 is a sectional view taken along line VI—VI of FIG. 5.
Figure 7:
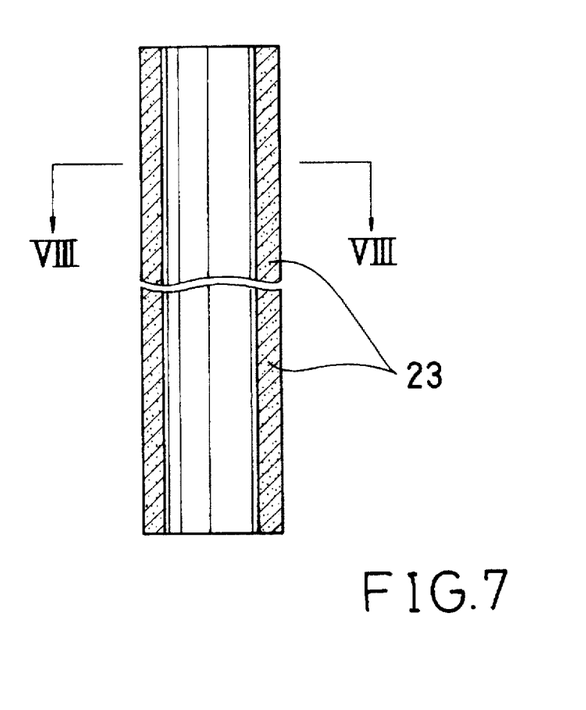
FIG. 7 is an enlarged vertically sectional view of a carrier body of the carrier member.
Figure 8:
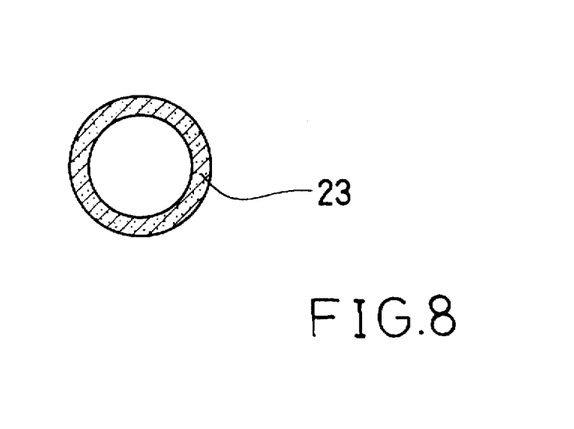
FIG. 8 is a sectional view taken along line VIII—VIII of FIG. 5.
Figure 9:
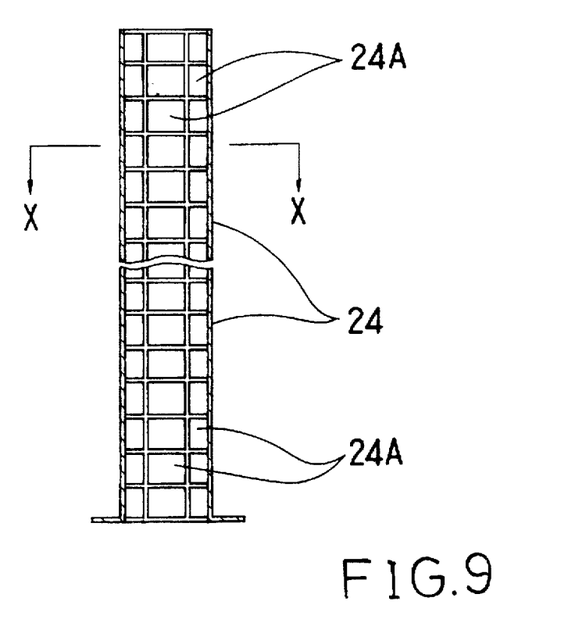
FIG. 9 is an enlarged vertically sectional view of an inner mesh sleeve of the carrier member.
Figure 10:
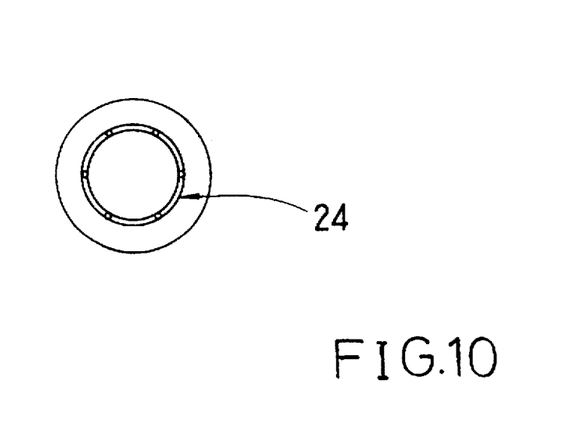
FIG. 10 is a sectional view taken along line X—X of FIG. 5.
Figure 11:
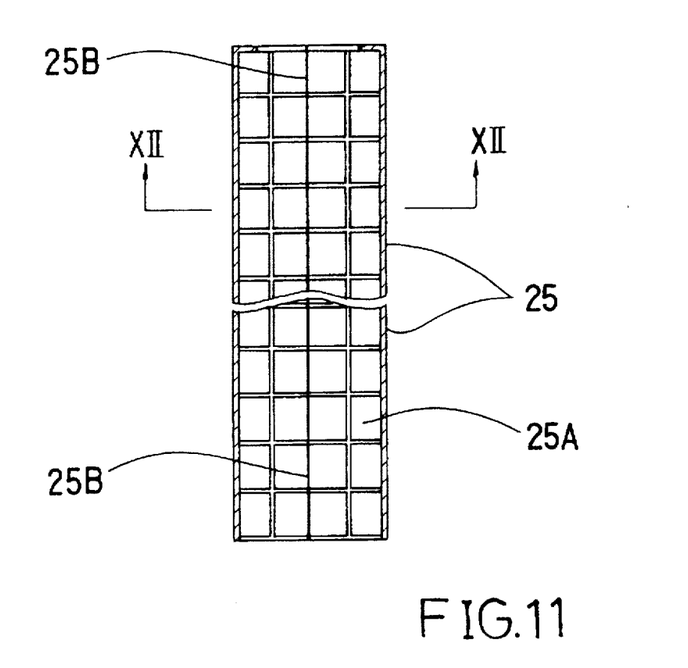
FIG. 11 is an enlarged vertically sectional view of an outer mesh sleeve of the carrier member.

As shown in FIG. 4, the upper support disk 35 is formed with a plurality of openings 35A corresponding to or vertically aligned to the fixture members 36. Each opening 35A has a diameter substantially equal to as the outer diameter of the carrier member 22 so as to closely receive an upper section of the carrier member 22. Further, each opening 35A may be modified to have a diameter smaller than the outer diameter of the carrier member 22 so as to more closely receive the upper section of the carrier member 22 therein. Also, each opening 35A may be provided with a spring member (not shown) so as to reliably receive the upper section of the carrier member 22 therein.

Each carrier member 22 is releasably retained on the upper and lower support disks 35 and 34 of the drive unit 32 by engaging the lower section thereof with the plug portion 36B of the fixture member 36 and by inserting the upper section thereof into the opening 35A of the upper support disk 35. The carrier member 22 is arranged in substantially parallel with the stem 33 since the fixture member 36 and the opening 35A are arranged in vertical alignment. As will be appreciated, the carrier member 22 can be easily replaced with a new one since it can be removed from the drive unit 32.

Figure 12:
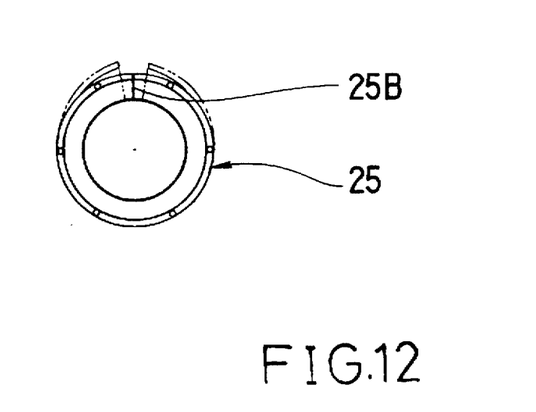
FIG. 12 is a sectional view taken along line XII—XII of FIG. 5.

As shown in FIGS. 5 to 12, the carrier member 22 is constituted essentially of a hollow cylindrical carrier body 23 formed of porous materials which may immobilize thereon the nonagglutinative microorganisms such as yeasts, a rigid inner mesh sleeve 24 as a reinforcement member having mesh openings 24A and fitted in a hollow portion of the carrier body 23, and a rigid outer mesh sleeve 25 as the reinforcement member having mesh openings 25A and sheathed on the carrier body 23. The porous materials for the carrier body 23 may be soft material such as open-cell rubber foam, nonwoven fabric and polypropylene fiber. As will be apparent, the carrier body 23 does not inherently have self-sustainability. The inner and outer mesh sleeves 24 and 25 may be formed of hard resins or other rustless materials. Further, the outer mesh sleeve 25 is formed with a longitudinal slit 25B extending over the entire length thereof so as to be flexibly expanded when it is incorporated in the carrier body 23 (FIG. 12). The inner and outer mesh sleeves 24 and 25 have sufficient self-sustainability due to rigidity thereof, thereby effectively sustaining the carrier body 23 so as not to be deformed.

The nonagglutinative microorganisms are immobilized on the carrier member 22 with a known method. Such a method is disclosed, for example, in Japanese Laid-Open Patent Publication No. 6-7163 entitled "Method of Immobilizing Nonagglutinative Microorganisms". As disclosed therein, first, a desired amount of activated carbon which may be suspended in water is provided. The activated carbon has diameters of from 10 to 2000 micrometer so as to be received in pores of the carrier body 23 and has pore diameters of from 3 to 100 micrometer. The activated carbon is then brought into contact with the nonagglutinative microorganisms in water so that the nonagglutinative microorganisms is immobilized in the pores thereof. Subsequently, the carrier member 22 is dipped in water containing the activated carbon immobilized with the nonagglutinative microorganisms so that the activated carbon immobilized with the microorganisms are filled in the pores of the carrier body 23. Thus, the nonagglutinative microorganisms are immobilized on the carrier member 22.

Further, in this embodiment, the carrier body 23 can be previously brought into contact with the activated carbon immobilized with the microorganisms before it is combined with the inner and outer mesh sleeves 24 and 25, if required.

Moreover, in this embodiment, although the inner cylinder 4 is used in the treatment tank 2, such an inner cylinder 4 may be removed, if required.

Figure 13:
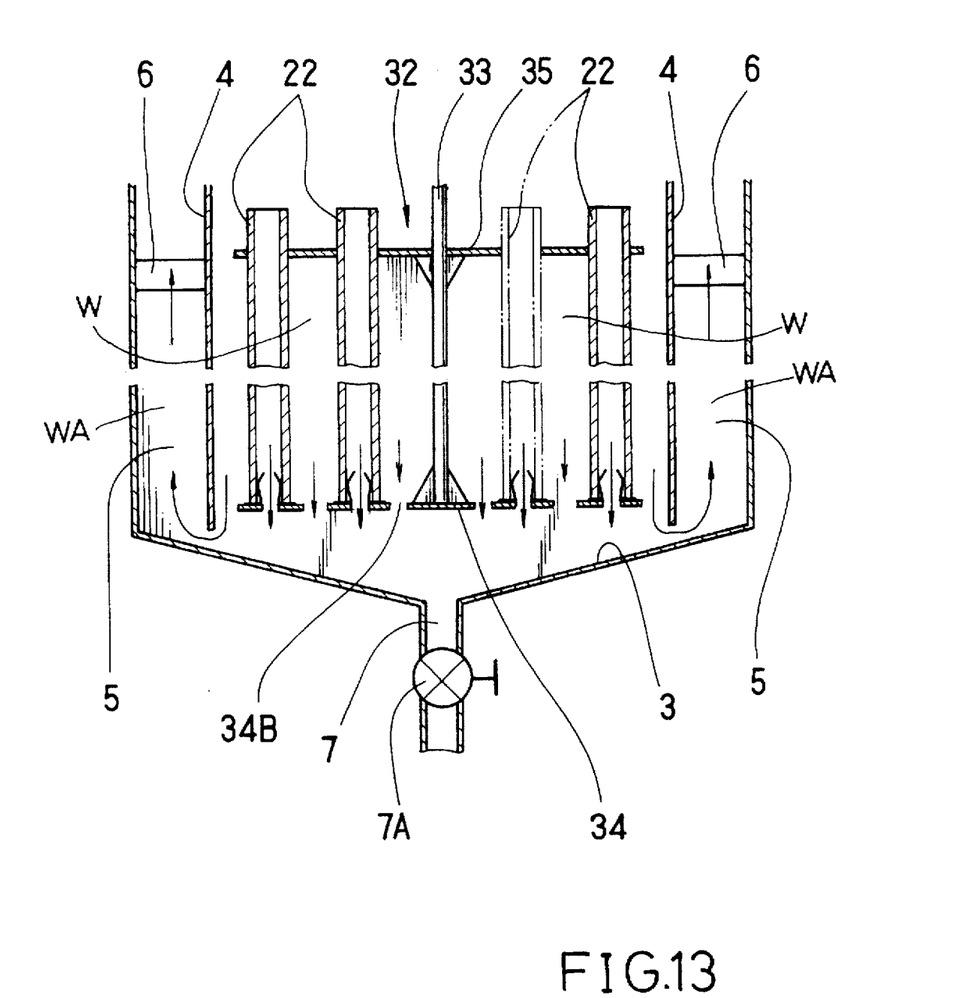
FIG. 13 is a partially enlarged schematic illustration of the bioreactor showing a mounting mechanism of the carrier member on the drive unit.

The operation of the bioreactor 1 will now be described with reference to FIGS. 1 and 13.

The liquid W to be treated is fed into the treating cavity 2a through the inlet port 14a at a room temperature or a predetermined desired temperature before the motor 15 is operated to rotate the drive shaft 16. When the drive shaft 16 is rotated, the stem 33 coupled to the drive shaft 16 through the coupling 17 is rotated about an axis thereof at a predetermined rotational speed, and simultaneously, the upper and lower support disks 35 and 34 mounted on the stem 33 are rotated at the rotational speed. As a result, the carrier members 22 retained on the upper and lower support disks 35 and 34 are rotated along orbital paths about the stem 33, thereby continuously and forcedly performing uniform contact between the microorganisms immobilized on the carrier members 22 and the liquid W in the treating cavity 2a. Thus, the liquid W is effectively treated by the microorganisms. Further, the carrier member 22 is smoothly rotated in the liquid W without accompanying deformation of the carrier body 23 since the carrier body 23 is supported by the inner and outer mesh sleeves 24 and 25. The microorganisms are stably immobilized on the carrier body 23 during rotation of the carrier body 22.

It is to be noted that the liquid W is usually continuously fed into the treating cavity 2a through the inlet port 14a in accordance with working capacity of the microorganisms. However, the liquid W may be intermittently fed into the treating cavity 2a so as to be sufficiently treated by the microorganisms.

The liquid W passes around the carrier members 22 and flows out to the bottom wall 3 through the passage holes 34B formed on the lower support disk 34 and a clearance between the inner cylinder 4 and the lower support disk 34. Further, a part of the liquid W passes through the carrier members 22 and flows out to the bottom wall 3 through the through holes 34A formed on the lower support disk 34 since the carrier member 22 has a tubular configuration. Thus, the liquid W flows downwardly in the treating cavity 2a while it effectively contacts the microorganisms on the carrier body 23 of the carrier member 22.

The liquid W delivered to the bottom wall 3 is introduced to the flow passage 5 as treated liquid WA. In the treated liquid WA, the pollutant materials or the organic stuff materials are effectively treated. The treated liquid WA is then led upwardly to the outlet channel 8. The treated liquid WA passes through the outlet port 8A and the hopper 9, and finally discharged through the conduit pipe 10.

According to the bioreactor 1 of the first embodiment, the microorganisms may uniformly contact the liquid W. This may lead increased contact efficiency between the microorganisms immobilized on the carrier members 22 and the liquid W.

Figure 17:
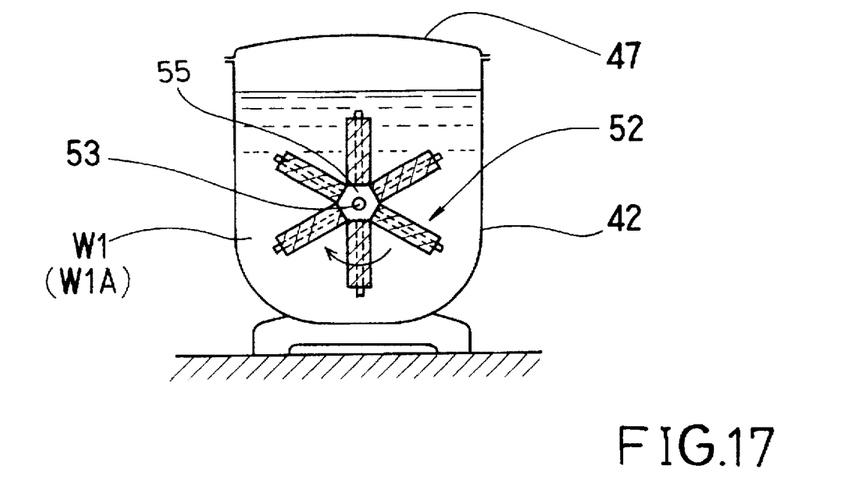
FIG. 17 is a sectional view taken along line XVI—XVI of FIG. 16.
Figure 18:
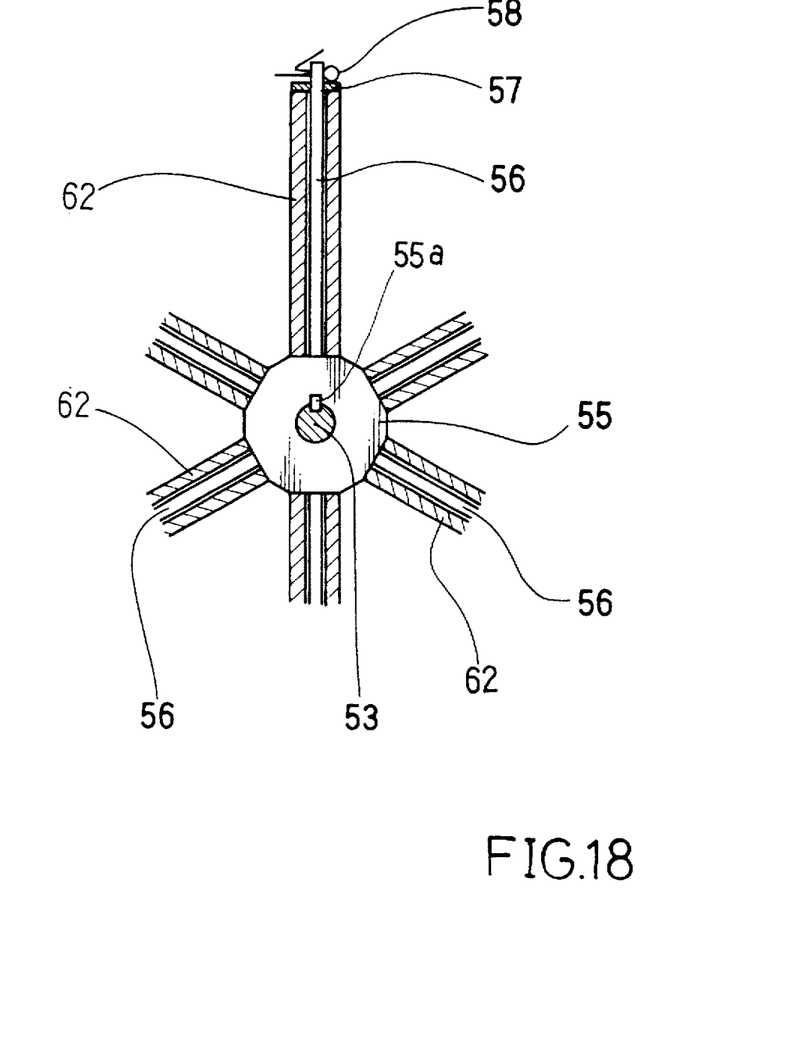
FIG. 18 is a partially enlarged schematic illustration of FIG. 17 showing a mounting mechanism of a carrier member on a drive unit.
Figure 19:
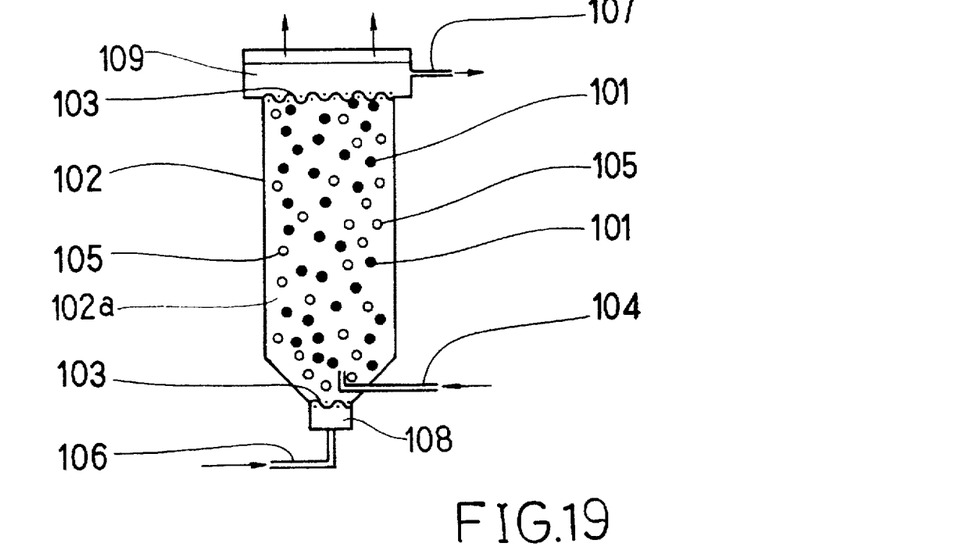
FIG. 19 is a vertically sectional schematic illustration of a conventional bioreactor.
Figure 20:
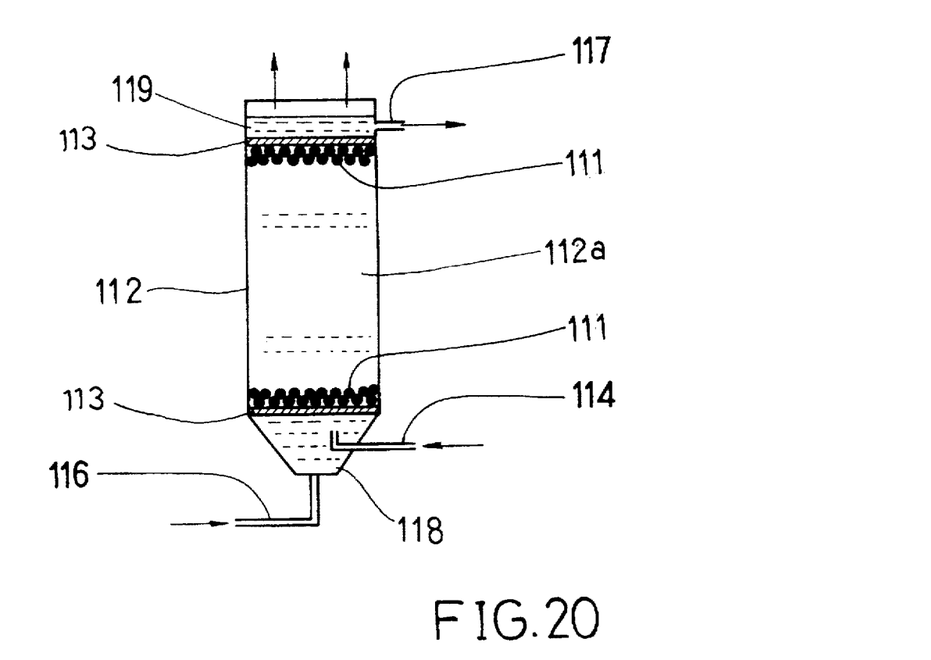
FIG. 20 is a vertically sectional schematic illustration of another conventional bioreactor.

Referring now to FIGS. 16 to 18, shown therein is a second embodiment of the invention. As shown in FIGS. 16 and 17, a bioreactor 51 is constituted mainly of a transversely elongated treatment tank 42 having a treating cavity 42a into which liquid W1 to be treated is introduced, a plurality of tubular carrier members 62 immobilized with microorganisms and located in the treating cavity 42a, a drive unit 52 for retaining the carrier members 62 and rotating the same in the treating cavity 42a. The treatment tank 42 has an inlet port 42A and an outlet port 42B and is detachably provided with a cover plate 47. The drive unit 52 includes a stem 53 as a support unit transversely received in the treating cavity 42a. The stem 53 penetrates opposed walls of the treatment tank 42 and is water tightly sealed by sealing members 43 mounted on the walls of the treatment tank 42. The stem 53 is also rotatably supported by bearing members 44. The drive unit 52 also includes an external motor 45 as a power unit which is coupled to the stem 53 through a gear unit 46.

The stem 53 is provided therealong with a plurality of mounting members 55 which are spaced at desired intervals by spacers 54 and which are unrotatably keyed on the stem 53 by key members 55a. Each mounting member 55 is fixedly provided with a plurality of radially extending support rods 56. Each support rod 56 is provided with a tubular carrier member 62 by engaging a hollow portion of the carrier member 62 with the support rod 56. As shown in FIG. 18, the carrier member 62 is detachably secured on the support rod 56 by utilizing a washer 57 and a split pin 58. Further, since the carrier member 62 has the same construction as the carrier member 22 in the first embodiment, the explanation of the carrier member 62 will be omitted.

The operation of the bioreactor 1 will now be described with reference to FIG. 16.

The liquid W1 to be treated is fed into the treating cavity 42a through the inlet port 42A before the motor 45 is operated. When the motor 45 is driven, the stem 53 coupled to the motor 45 through the gear unit 46 is rotated about an axis thereof at a predetermined rotational speed. As a result, the carrier members 62 retained on the stem 53 are rotated about the stem 53, thereby continuously and forcedly performing uniform contact between the microorganisms immobilized on the carrier members 62 and the liquid W1 in the treating cavity 42a. Thus, the liquid W1 is effectively treated by the microorganisms.

The liquid W1 passes around the carrier member 62. The liquid W1 is then led to the outlet port 42B as the treated liquid W1A, and finally discharged through the outlet port 42B.

Like the bioreactor 1, according to the bioreactor 51 of the second embodiment, the microorganisms may uniformly contact the liquid W1. This may increase contact efficiency between the microorganisms immobilized on the carrier member 62 and the liquid W1.

In the first and second embodiments, the drive unit is designed such that the stem is rotated about the axis thereof. However, the drive unit can be modified in such a way that, for example, the stem is eccentrically rotated by utilizing an eccentric coupling (not shown) or the like. Moreover, the drive unit can be modified in such a way that, for example, the stem is reciprocally moved in longitudinal directions, transverse directions, or combined directions thereof by utilizing a crank shaft (not shown) of the like.

The preferred embodiments herein described are intended to be illustrative of the invention and not to limit the invention to the precise form herein described. They are chosen and described to explain the principles of the invention and their application and practical use to enable others skilled in the art to practice the invention.

What is claimed is:

1. A bioreactor comprising a treatment tank for receiving liquid to be treated, at least one carrier member having a carrier body formed of a porous deformable material and having immobilized thereon nonagglutinative microorganisms for treating the liquid, and a drive unit for moving said at least one carrier member in said treatment tank, said drive unit comprising a power unit and a support member coupled thereto and comprising a stem connected to said power unit and a support disk mounted on said stem and retaining said at least one carrier member thereon and substantially perpendicular thereto, said stem and support disk being rotated when said power unit is energized, thereby moving said at least one carrier member along an orbital path about said stem, said at least one carrier member having a tubular shape so as to pass liquid therethrough and comprising a reinforcing member to prevent deformation of said carrier body.

2. The bioreactor as defined in claim 1, wherein said at least one carrier member is plural in number, said carrier members being arranged in substantially parallel with said stem.

3. The bioreactor as defined in claim 1, wherein said at least one carrier member is detachably connected to said support disk.

4. A bioreactor according to claim 1, wherein the reinforcing member is a tubular mesh disposed internally of said carrier body.

5. A bioreactor according to claim 4, additionally comprising a second reinforcing member comprising a tubular mesh disposed externally of said carrier body.

6. A bioreactor comprising a treatment tank for receiving liquid to be treated, at least one carrier member having a carrier body formed of a porous deformable material and having immobilized thereon nonagglutinative microorganisms for treating the liquid, and a drive unit for moving said at least one carrier member in said treatment tank, said drive unit comprising a power unit and a support member coupled thereto, said support member including a stem coupled to said power unit and retaining said at least one carrier member thereon, said stem being rotated when said power unit is energized, thereby rotating said at least one carrier member around said stem, said at least one carrier member being tubular in shape, extending radially from the rotated stem and including a reinforcing member to prevent deformation of said carrier body.

7. The bioreactor as defined in claim 6, wherein said at least one carrier member is plural in number, said carrier members being radially directed on said stem.

8. The bioreactor as defined in claim 6, wherein said at least one carrier member is detachably connected to said stem.

9. A bioreactor according to claim 6, wherein the reinforcing member is a tubular mesh disposed internally of said carrier body.

10. A bioreactor according to claim 9, additionally comprising a second reinforcing member comprising a tubular mesh disposed externally of said carrier body.

* * * * *